(12) United States Patent
Zmood et al.

(10) Patent No.: US 8,186,587 B2
(45) Date of Patent: May 29, 2012

(54) TAGGING METHODS AND APPARATUS

(75) Inventors: Ronald Barry Zmood, Victoria (AU); Jason Chaffey, Victoria (AU)

(73) Assignee: Bluechip Limited, Victoria (AU)

( * ) Notice: Subject to any disclaimer, the term of this patent is extended or adjusted under 35 U.S.C. 154(b) by 951 days.

(21) Appl. No.: 12/153,778

(22) Filed: May 23, 2008

(65) Prior Publication Data
US 2008/0296373 A1   Dec. 4, 2008

Related U.S. Application Data

(63) Continuation-in-part of application No. PCT/AU2007/001799, filed on Nov. 23, 2007.

(60) Provisional application No. 60/860,795, filed on Nov. 24, 2006.

(51) Int. Cl.
  *G06F 19/00* (2006.01)

(52) U.S. Cl. ...................................... 235/385

(58) Field of Classification Search .................. 235/383, 235/385, 492; 340/10.1, 572.1
See application file for complete search history.

(56) References Cited

U.S. PATENT DOCUMENTS

| | | | |
|---|---|---|---|
| 3,967,161 A | 6/1976 | Lichtblau | |
| 3,985,318 A | 10/1976 | Dominey et al. | |
| 4,510,490 A | 4/1985 | Anderson, III et al. | |
| 5,420,569 A | 5/1995 | Dames et al. | |
| 5,481,102 A | 1/1996 | Hazelrigg, Jr. | |
| 5,552,778 A | 9/1996 | Schrott et al. | |
| 5,563,583 A | 10/1996 | Brady et al. | |
| 5,565,847 A | 10/1996 | Gambino et al. | |
| 5,812,065 A | 9/1998 | Schrott et al. | |
| 6,060,815 A | 5/2000 | Nysen | |
| 6,255,949 B1 | 7/2001 | Nicholson et al. | |
| 6,819,246 B1 | 11/2004 | Seppa | |
| 7,362,228 B2 * | 4/2008 | Nycz et al. | 340/572.1 |
| 7,602,284 B2 * | 10/2009 | Wong et al. | 340/539.22 |
| 2006/0109118 A1 | 5/2006 | Pelo et al. | |
| 2006/0214791 A1 | 9/2006 | Tethrake et al. | |
| 2007/0132593 A1 | 6/2007 | Yamazaki | |
| 2007/0284428 A1 * | 12/2007 | Cambre et al. | 235/375 |

FOREIGN PATENT DOCUMENTS

| | | |
|---|---|---|
| GB | 2 149 275 A | 6/1985 |
| JP | A-08-293012 | 5/1996 |
| WO | WO 2004/083798 A1 | 9/2004 |
| WO | WO 2004/084131 A1 | 9/2004 |
| WO | WO 2006/086409 A2 | 8/2006 |

OTHER PUBLICATIONS

*New RFID Tag Withstands Industrial Sterilization*; RFID Update; Dec. 13, 2006; http://www.rfidupdate.com/articles/index.php?id=1261.

(Continued)

*Primary Examiner* — Seung Lee
(74) *Attorney, Agent, or Firm* — Oliff & Berridge, PLC

(57) ABSTRACT

A method of tagging and sterilizing an item, the method including the steps of: providing an item (12) that is to be sterilized and tagged; applying an RFID tagging device (22) to said item, said tagging device including a data store (30) formed from an array of micromechanical resonant members (34), said resonant members being configured to vibrate in accordance with an applied RF signal, so as to provide a data response; and sterilizing said tagged item by autoclaving and/or by irradiation.

20 Claims, 4 Drawing Sheets

OTHER PUBLICATIONS

Gamma Radiation Resistant RFID Tags; Jan. 29, 2007; http://web.archive.org/web/20070129144354/http://www.advantapure.com/gamma-rfid-tags.htm.

Wang et al., "Frequency Trimming and Q-Factor Enhancement of Micromechanical Resonators Via Localized Filament Annealing," Transducers '97, 109-12, IEEE (1997).

Cleland et al., "Fabrication of High Frequency Nanometer Scale Mechanical Resonators from Bulk Si Crystals," 69 Appl. Phys. Lett., 2653-2655, (Oct. 28, 1996).

Greywall, "Micromechanical RF Filters Excited by the Lorentz Force," J. Micromech. Microeng. 9 78-84 (1999).

Cleland, "Foundations of Nanomechanics From Solid-State Theory to Device Applications," Oct. 18, 2002, Springer Verlag, pp. 303-319, and 426-427 (footnotes).

Elwenspoek et al., "Mechanical Microsensors," Jan. 12, 2001, $1^{st}$ Ed., Springer Verlag, pp. 121-126, 257-258, and 279, 280 and 286 (footnotes).

\* cited by examiner

TAGGING METHODS AND APPARATUS

The present invention relates to tagging methods and apparatus. It relates particularly to the tagging of items that have to undergo physical sterilization or be subjected to ionizing radiation.

In order to identify items such as surgical instruments, it is known to assign them a serial number, a barcode or a data matrix (a 2D barcode). This number or code may be engraved into the instruments or added to them as labels, and can be used in their inventory management. This inventory management can still however be labour intensive, as even though a barcode may be machine readable, it requires line-of-sight reading, and for example will generally need to be manually held in a suitable reading position. Further, barcodes that are printed on address labels are known to delaminate on exposure to harsh environments such as motors. Other barcodes can be screwed on, but the barcode pattern can degrade with time or even be removed.

RFID tags have started to replace barcodes in some applications, and have a number of advantages. For example, RFID tags do not require line-of-sight reading, are quick to read, may hold more information than a barcode, and may be read/write devices. RFID tags generally comprise a microprocessor for holding data and an antenna for communications with an RFID interrogator through an RF interrogation signal. The tags may be passive, in which case they receive their power from the interrogation signal, or may be active, in which case they include a battery.

Clearly, it would be useful if RFID tags could be applied to surgical instruments and the like. Unfortunately, however, surgical instruments and other medical and healthcare items generally need to undergo rigorous physical sterilization procedures that include heat sterilisation, such as steam sterilisation, and/or radiation sterilisation, for example by application of gamma irradiation.

This can be problematic when attempting to provide RFID tagging, as standard RFID tags are unable to withstand such physical sterilization regimes. It might be possible to apply RFID tags after an item has been sterilized, or to make the tags removable so that they do not themselves need to undergo sterilization. Such solutions are however not always practicable, and can present their own problems, e.g. a lack of tag-item integrity and the possibility of errors in replacing the tags.

Attempts have been made to provide heat-resistant tags by encasing them in protective packaging in the form of thermal insulation. This however may make the tags too large for many uses, and will generally also not protect gamma irradiation. RFID tags have been developed to withstand some gamma irradiation, but such tags are expensive, as special manufacturing techniques are needed for the CMOS circuitry. Also, such tags may still not be robust enough to withstand irradiation levels needed for an effective physical sterilization process.

One aspect of the present invention provides a method of tagging and sterilizing an item, the method including the steps of:

provinding an item that is to be sterilized and tagged;

applying an RFID tagging device to said item, said tagging device including a data store formed from an array of micromechanical resonant members, said resonant members vibrating in accordance with an applied RF signal, so as to provide a data response; and sterilizing said tagged item by autoclaving and/or by irradiation.

Autoclaves may for example apply pressurised steam to the tagged item at a temperature of over 120° C. for an appropriate period of time, e.g. at 121° C. for 15 minutes or at 134° C. for 3 minutes. Irradiation could be gamma ray irradiation, e.g. at a dosage in excess of about 2.5 Mrads. Irradiation may also take other forms, e.g. beta ray irradiation (i.e. electrons). It will be appreciated that other temperature, time and irradiation dosage regimes are possible, and that the regimes will be set so as to ensure that sterilization of an item occurs appropriately.

The micromechanical resonant members are fabricated using MEMS technology (microelectromechanical systems technology), which is also known as MST (Micro System Technology) and micromachining. MEMS technology includes fabrication technologies for integrated circuits, and technologies specifically developed for micromachining. It generally relates to the fabrication of components with dimensions in the range of micrometers to millimeters. MEMS techniques may include for example masking, deposition and etching steps, amongst other well-known lithographic and micromachining processes. It may include for example photolithography and thin film deposition or growth. Typically, the process results in a laminate structure. A number of structural layers can be formed on a substrate, and required components can be formed by selective etching of the substrate and/or sacrificial materials and component materials deposited thereon. The resulting micromachined components may be combined with electronics that are fabricated using standard integrated circuit processes.

The resonant members of the array may take the form of cantilever or bridge structures, and may have different resonant frequencies from one another so that they may respond to different frequency components of an excitation/interrogation signal. The presence or absence of a resonant member of a particular frequency and its ability to vibrate may be equated to a logical "1" or "0", and may represent a binary code, a status flag or the like. A determination of the presence or absence of a vibratable member may be made by applying an excitation signal to the array at a number of different frequencies, and by analysing a response to determine if it is indicative of a resonant member of a particular frequency.

Data may be encoded into these arrays in a number of ways, e.g. by fabricating members only of particular frequencies, by making members with a full range of frequencies and by then destroying particular members, or by enabling or disabling the ability of particular members to vibrate, e.g. by using a removable tether such as a fusible link.

The present invention enables items such as surgical instruments, prostheses and other medical and healthcare items, to be tagged in an RFID readable manner whilst still enabling them to undergo rigorous physical sterilization protocols. This is because the resonant members themselves are able to withstand high temperatures and high levels of irradiation, and the use of the resonant members as data storage devices can remove the need for vulnerable microprocessors, memory and associated circuitry.

The tagging system has major advantages, as it allows such items to be identified in a non-line of sight manner and without human intervention. It may therefore facilitate automated item management and tracking, and also allows items to be read whilst within a container or sterile wrapper or within the body. In this latter regard, the use of the resonant member tags also facilitates the provision of a biocompatible tag.

Resonant members that may be used in the present invention are disclosed in WO 2004/084131 and WO 2004/083798, both to the inventor of the present application. The former describes a number of possible resonant member constructions, whilst the latter discloses sensing devices that may record temperatures and the like, and may provide added benefit to the tagging system by allowing temperature tracking and the like.

Resonant members are also disclosed in U.S. Pat. Nos. 5,481,102, 5,552,778, 5,563,583, 5,565,847 and 6,819,246, and the contents of these documents, and of WO 2004/084131 and WO 2004/083798, are incorporated herein in their entirety by reference.

A particularly preferred form of resonant member is one that vibrates under the Lorentz force. This has the advantage of simple construction, and also may be used with irradiation hard support circuitry, e.g. signal coupling circuitry. For example, the micromechanical resonant members may be associated with a simple antenna and conductor circuit.

As well as signal coupling circuitry, the support circuitry may include addressing circuitry, e.g. for programming or encoding the array, e.g. by fusing tethers that hold the resonant members against vibration. This addressing circuitry may also be autoclave and gamma-ray resistant, and in one preferred form includes a diode addressing array, where the diodes are formed as Schottky diodes. The support circuitry may also include resistors, capacitors and inductors. The addressing array may for example take a form as disclosed in co-pending International Patent Application PCT/AU2007/001800 entitled "Addressing Apparatus and Methods".

By providing support circuitry, e.g. an address array, in a form that can survive the sterilization processes, it allows for encoding of data after sterilization, and so provides for a versatile system. It would also be possible, however, to encode the array of micromechanical members prior to sterilization, in which case the address array may not be designed to withstand the sterilization process, as it may not be needed further after the initial encoding.

Encoding need not use an addressable array, and could occur for example by fabricating only certain resonant members, by destroying certain resonant members, and/or by removing restraining tethers using a numerically controlled laser beam or a laser beam and mask.

The micromechanical resonant members may be provided in vacuum compartments in an array housing or the like, which may then be packaged within a protective casing. The casing may also enclose an antenna, which may be separate from the housing. The protective casing is preferably chosen to be autoclave and/or irradiation resistant to the appropriate degree for the application, e.g. to survive a one time sterilization or multiple sterilizations.

The resonant member array may for example be made on a silicon substrate with a silicon cover, and may be encased in a heat and radiation resistant polymer.

The RFID tag may be incorporated into the tagged item in any suitable manner, and may be included in the item during or after manufacture. It may for example be adhered to the item, moulded with the item or mechanically fastened to the item by a fixing element of some type. The method of attachment should resist failure due to autoclaving or irradiation. The item may be tagged directly and/or a tag may be applied to a container or wrap in which the item is provided.

The tagged item may be any item that must be both tagged and sterilized through an irradiation and/or autoclave process. It may be a medical or healthcare device, instrument, or supply. It may be a surgical instrument, including dental or veterinarian instruments, an implant, such as a prothesis, a syringe, e.g. a prefilled sterile pack, a blood product container or the like. It could also take the form of a food product or other hygiene related item, and could be used with scientific instruments, e.g. to avoid contamination problems.

In one especially advantageous application, the present invention may provide a loaner kit, e.g. a prothesis loaner kit, wherein elements of the loaner kit are tagged using micromechanical arrays of resonant members that provide a data response to an interrogation signal.

Loaner kits typically comprise a number of elements for use in a surgical procedure, and are provided to a hospital on a loan basis, with the hospital paying for the parts of the kit that they use and returning the kit to the provider once the procedure is complete. A loaner kit may include a very large number of parts, all of which need to be tracked through the loaner process, which may include a supply stage, sterilization stages, a surgery stage, and a return stage.

A loaner kit is often used for example during prosthetic surgery, and, as a surgeon often does not know exactly what size joint or the like a patient needs until an exploration of the implantation site has been made, an orthopaedic loaner kit may need to include a variety of types and sizes of implant and also a set of specialised instruments for each of these implant sizes for fixing them accurately into place, e.g. jigs, saws, boring tools, reamers and the like.

When a prothesis operation is to be performed, a surgeon will estimate the size and possibly type of prothesis required, and will order a kit accordingly from a prothesis provider. The provider will then make up a kit in accordance with the surgeon's requirements, and will send the kit out to the hospital. At the hospital, the kit is opened in the theatre, and the surgeon uses the required pieces of equipment, e.g. once exact sizes and the like have been established through an inspection of the implant site. After surgery, the parts of the kit, including unused prostheses and used and unused tools, are bundled back into the kit container and returned to the kit provider. The kit provider will then sterilize the kit, before inventorying and storing the kit parts for further use in a new kit.

At present, part identification and storage is carried out manually. This is labour intensive. Also, as it can be difficult to tell apart similar components of slightly different sizes, the possibility for errors and misidentification is high. This could have major implications, e.g. in the inability to perform an operation or in the incorrect implantation of a device. Accordingly, kit make-up is subject to a number of checking and verification processes that can further increase costs.

By using the present RFID tag system, however, the pieces of the kit can be read wirelessly in a quick and accurate manner, so that missing parts and misidentification can be to a large extent eliminated. The system may check for the presence of parts, confirm matches, dispatch and receive parts, and bills appropriately. The system may check part histories, and may check that all parts have been sterilized, e.g. by scanning at various points in the process. Further, RFID readers in the theatre may allow a surgeon to confirm exactly what parts are in a kit before a procedure starts, and can also be used to ensure that no items are left behind. It can further track which items have been used with which patients, in case an infection protocol needs to be instigated, e.g. to recall and destroy or sterilize items that have been used on a particular patient and that may potentially be infected.

Typically, instruments are sterilized in bulk on an instrument tray, basket or some other type of container, and preferably, these containers are tagged as well. The container tags may also utilise resonant member arrays, but in one form may include a transponder to read the tags of instruments provided on the tray. In this case, the container tag may be provided in a thermal housing that protects the transponder and associated circuitry during autoclaving, and may also be an active tag and be provided with a battery. This may require the tag to have a somewhat larger form than the resonant member tags used on the actual instruments, but this is possible because the container itself will generally be quite large, and because the containers generally only need to undergo autoclaving operations, and not gamma irradiation.

Alternatively, the container tags could be removable from the containers during the autoclaving or a gamma irradiation. This is less prone to problems than having removable tags for the surgical instruments, as again the container tags can be larger and so more easily handled, and may include for example observable markings for ensuring correct replacement of the tags. Also, it may not be as critical to correctly tag the containers, as the instrument tags will still be correct, and an associated management system could track the instruments on the containers and alert when a change has occurred due to incorrect replacement of a container tag.

Accordingly, a particularly useful tagging system for autoclave and possibly irradiation sterilization includes a set of items tagged using passive tags that include micromechanical resonant members, and a tagged item container, the container tag being an active tag that is able to read the tags of the items associated with the container. An information system may therefore receive information on the items in the container through the container tag, rather than have to read the individual item tags, which may not actually be possible, e.g. due to short read ranges for the passive tags.

Another aspect of the invention provides a system of tracking RFID tagged items through a process that includes the sterilization of the tagged items by an autoclave or irradiation process, the system including an inventory controller in communication with one or more RFID readers for reading the tagged items, wherein the items are tagged by RFID devices, and wherein the RFID devices include data stores formed by micromechanical resonant members that respond to an applied RF interrogation signal with a data response.

The present invention extends to sterilized and RFID tagged items provided through any of the above methods, and, viewed from another aspect, provides a sterilized and RFID tagged item, wherein said RFID tag includes a data store formed from an array of micromechanical resonant members that are configured to vibrate in accordance with an applied RF interrogation signal, so as to provide a data response; and wherein the sterilization was by autoclaving and/or by irradiation of said tagged item whilst said item was tagged.

The provision of a tagged loaner kit is itself especially advantageous, and, viewed from a further aspect, the present invention provides a method for providing a prothesis loaner kit, the method including:

tagging parts for use in loaner kits with RFID tags, said tags including micromechanical resonant members as data storage elements, said resonant members configured to vibrate in accordance with an applied RF interrogation signal so as to provide a data response;

storing information regarding said tagged parts in a database;

constructing a kit of parts according to a kit list; and checking said parts against said list by scanning said tags.

The items may be surgical instruments, implants and other required parts, and tags may be read in order to identify items for placing in a kit and to confirm that items match, e.g. that implants and instruments are of corresponding size and the like. The tags may be read to track a kit through a loan process. The method may include any of the steps of: reading tags to check that items and containers have been sterilized, e.g. at a hospital prior to and after a procedure or when returned to a loan kit provider; and reading of kit parts when received by the hospital and/or provider and when in the surgery room, e.g. to check that required items are present or to identify where they are in the kit. The identification and location of parts in the surgery may be especially advantageous as the surgeon may not know which of the elements they need and the sizes until they have surgically examined the implant site.

An inventory management system may be provided in each location where a check on the kit is necessary, and may be linked to one or more central databases for tracking tagged items and for recording their usage details, e.g. including e.g. the number of times they have been used and the patients with which they have been used.

The method may include the tagging a container in which items of the kit are provided, and may include the tagging of a tote in which the items and item containers are shipped. The container tags may be able to read the items within them, and the tote tags may be able to read the container tags and/or item tags.

The present invention is also suitable for use in the tagging of items that are subject to ionizing radiation but in a non-sterile environment.

By way of illustration, x-ray inspection systems are used to detect flaws in the internal construction of automotive tyres, sections of railway track, propeller shafts, turbine blades and other items including metallurgical components. It is often necessary to affix a tag to items, in order that the item can be identified during the inspection process. However, electronic RFID tags including a microprocessor and associated data storage device are unsuited to this application. The x-rays used during the inspection process cause damage to or the malfunctioning of the electronic components on the RFID tag.

In addition to x-rays, examples of ionizing radiation include, but are not limited to, energetic beta particles, neutrons and alpha particles. The ability of light waves (photons) to ionize an atom or molecule varies across the electromagnetic spectrum. X-rays, gamma rays and far ultraviolet light will all ionize many atoms and molecules in electronic circuitry, whilst very few atoms or molecules will be ionized by visible light and microwaves.

Two fundamental damage mechanisms take place, namely lattice displacement and ionization effects. Lattice displacement is caused by neutrons, protons, alpha particles, heavy ions, and very high energy gamma photons. They change the arrangement of the atoms in the lattice, creating lasting damage, and increasing the number of recombination centers, depleting the minority carriers and worsening the analog properties of affected semiconductor junctions.

Ionization effects are caused by charged particles, including the ones with energy too low to cause lattice effects. The ionization effects are usually transient, creating glitches and soft errors, but can lead to destruction of the device if they trigger other damage mechanisms, such as a latch-up. Photocurrent caused by ultraviolet and x-ray radiation may belong to this category as well. Gradual accumulation of holes in the oxide layer in MOSFET transistors leads to worsening of their performance, up to device failure when the dose is high enough.

The presence of ionizing radiation would also be a particularly serious problem in designing electronic RFID tags to identify items subject to ionizing radiation in non-sterile environments, such as items intended for use with or forming at least part of artificial satellites, spacecraft, aircraft, nuclear power stations and nuclear weapons. Manufacturers of electronic RFID tags for use in such non-sterile environments would therefore need to employ various methods of radiation hardening to use such tags. These methods are generally expensive and not always reliable.

Accordingly, another aspect of the invention provides a method of identifying an item, the method including the steps of:

applying an RFID tagging device to the item, said tagging device including a data store formed from an array of micromechanical resonant members, said resonant members being configured to vibrate in accordance with an applied RF signal, so as to provide a data response;

subjecting the item to ionizing radiation in a non-sterile environment; and reading the data response from the RFID tagging device.

The ionizing radiation may include any one or more of x-rays, gamma rays, beta particles, neutrons and alpha particles.

Yet another aspect of the invention provides a system of tracking RFID tagged items through a process in which subjecting each item is subject to ionizing radiation in a non-sterile environment, the system including an inventory controller in communication with one or more RFID readers for reading said tagged items, wherein said items are tagged by RFID devices, and the RFID device including a data store formed by micromechanical resonant members that respond to an applied RF interrogation signal with a data response.

A still further aspect of the invention provides a system of inspecting an item, including:

a radiation emitter for applying ionizing radiation to the item;

a radiation analyser for receiving and analysing radiation applied to the item; and a system of tracking RFID tagged items as described hereabove.

It should be noted that any one of the aspects mentioned above may include any of the features of any of the other aspects mentioned above and may include any of the features of any of the embodiments described below, as appropriate.

Embodiments of the present invention will now be described, by way of example only, with reference to the accompanying drawings. It is to be understood that the particularity of the drawings does not supersede the generality of the preceding description of the invention.

Figure 1:
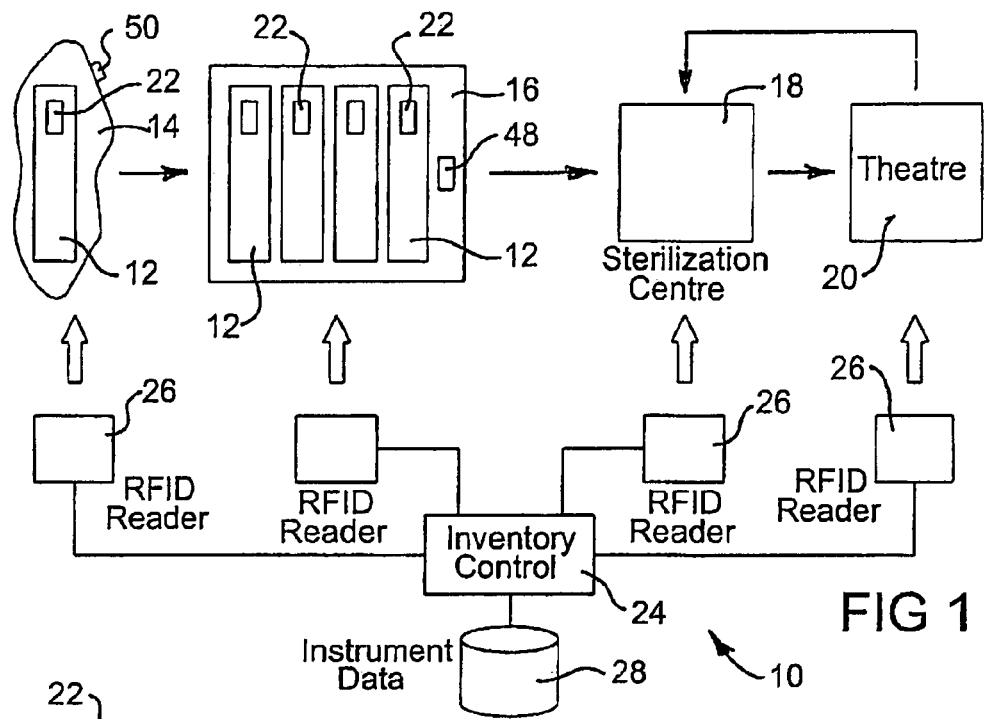
FIG. 1 is a schematic diagram of an inventory management system and tagged items.

FIG. 1 shows schematically an RFID inventory management system 10 for tracking tagged items in an environment where the tagged items need to be subject to rigorous physical sterilization regimes, i.e. an autoclave and/or an irradiation process, e.g. gamma ray irradiation or possibly beta ray irradiation. The system 10 is shown applied to surgical instruments 12 in a hospital environment.

The surgical instruments 12 may be autoclaved and/or irradiated at the manufacturers, e.g. to provide a new surgical instrument 12 in sterile packaging 14 that the hospital may purchase. The surgical instruments 12 are also autoclaved and/or irradiated after every use, and may be placed on an instrument tray 16 for ease of handling and to bulk sterilize the instruments. A hospital may include a central sterilization department 18, generally known as a CSSD (Central Sterile Supply Department) where all instruments and the like are sterilized before and after use, e.g. in a surgical theatre 20.

The inventory management system 10 tracks the instruments 12 throughout their life cycle and can monitor when the instruments 12 have been sterilized and how many times and with which patients they have been used. This may be done by tagging the instruments with RFID tags 22 and by having a central inventory control 24 in communication with tag interrogators 26 provided at appropriate locations in the hospital, e.g. in the sterilization centre 18 and the theatre 20. Thus, the purchase of new instruments, instances of sterilization of an instrument 12 and instances of use of an instrument in a theatre can all be registered by the appropriate interrogators 26, and an instrument's history can be recorded by the central control 24 in a database 28.

Such a system has a number of advantages in inventory control and in infection management, but is only made possible by providing an RFID tag 22 that can withstand the autoclave and/or irradiation sterilization regimes. Such regimes would include autoclaving at temperatures in excess of 120° C., e.g. at 121° C. for about 15 minutes or at 134° C. for about 3 minutes. It would also include gamma ray irradiation with doses in the region of 2.5 Mrads. Irradiation regimes may also include the use of beta (electron) irradiation.

Figure 2:
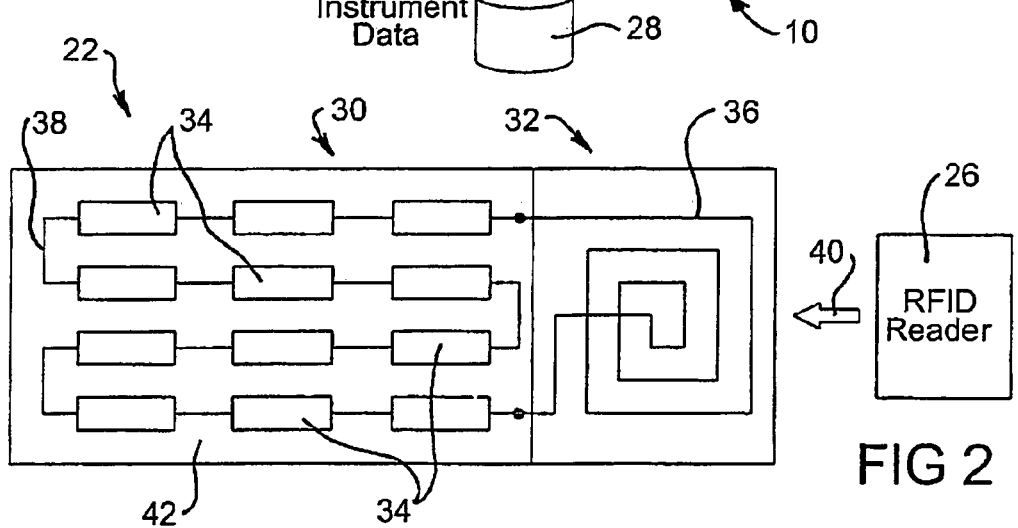
FIG. 2 is a schematic diagram of a tagging device.

The present system is provided through the use of RFID tags 22 that have data arrays formed of micromechanical resonant members. Such a tag is shown in FIG. 2, in which a tag 22 for use in a tagging and sterilization process comprises a data portion 30 and a support circuitry portion 32. The data portion 30 comprises an array of resonant members 34 that have different resonant frequencies from one another and that are connected to the support circuitry 32, including an antenna 36, by a common conductor 38.

In use, an RFID reader/interrogator 26 applies an excitation signal 40 to the antenna 36, and this induces ac current in the conductor 38. If the frequency of the ac current corresponds to the resonant frequency of a resonant member 34, the resonant member 34 will vibrate. This causes a corresponding change in impedance of the antenna circuit 32 that is reflected back to the interrogator 26. Thus, if a swept frequency interrogation signal or the like is applied to a tag, the tag responses can be used to identify which resonant members 34 exist and are free to vibrate, and the system can derive data from this. For example, at any particular frequency, the vibration of a resonating member 34 may indicate a "1" and the absence may indicate a "0".

Thus, the tag 22 may be encoded by making only certain ones of the resonant members 34 or by making them all and by then destroying selected members or by enabling or disabling them for vibration. For example, the resonant members 34 may be held against vibration by tethers, and may be encoded by removing selected tethers to allow selected ones of the resonant members 34 to vibrate. The resonant members 34 could also represent other data, e.g. status flags or the like.

The resonant members 34 could be bridge and/or cantilever structures, and could have tethers that are fusible by laser ablation, an electrical current or in some other manner. They could take any of the forms discussed in WO 2004/084131 and WO 2004/083798.

In one preferred form, the resonant members 34 are vibrated by the Lorentz force, and the excitation signal is applied to the resonant members 34 at the same time as a magnetic field is applied perpendicularly to the accurrent induced in the conductor 38. The field could for example be applied externally or internally by magnetic elements mounted in the tag 22.

Figure 3:
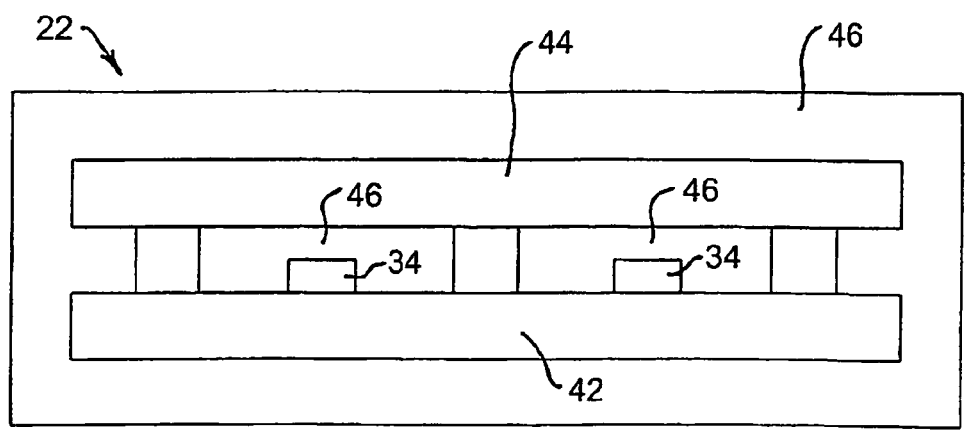
FIG. 3 is a schematic section through a tagging device.

The resonant members 34 may be formed on a silicon substrate 42, which, as shown in FIG. 3, may be bound to a further silicon substrate 44 to form vacuum enclosures 46 for the resonant members 34. The whole silicon structure and the support circuitry 32 may be placed within a protective housing 46 for both protection and handling purposes.

The use of the resonant members 34 as data carriers allows the RIFD tags 22 to withstand both autoclaving and irradiation sterilization, whilst remaining compact in size and allowing for RF communication. It does away with the need for vulnerable microprocessors and CMOS circuitry.

The protective housing 46 and the elements used in the construction of the supporting circuitry 32 are also able to be made autoclave and irradiation resistant. Thus, the protective housing that encases the silicon housing may be made from suitably robust forms of epoxy or other polymer materials, and the support circuitry 32 may merely comprise the antenna 36 and a conductor.

The support circuitry 32 may also comprise addressing circuitry or the like for the resonant members 34, e.g. to program the device and fuse the resonant member tethers, e.g. as discussed in the co-pending patent International Patent Application PCT/AU2007/001800 entitled "Addressing Apparatus and Methods". Such circuitry too may be made autoclave and irradiation resistant, and may for example use Schottky diodes, as well as other active and passive electronic components that are intrinsically radiation hard. This may also include resistor, capacitor and inductor circuitry.

As well as tagging the surgical instruments 12, instrument trays 16 or other sterilization containers or baskets may also be provides with an RFID tag 48. The instrument tray tag 48 may itself be able to read the tags 22 of the surgical instruments 12 that are in the tray 14, the contents of which are incorporated herein by reference in their entirety. This then allows the details for the surgical instruments 12 to be read via the tray tag 48, which may for example provide a greater reading range or may simply be more easily accessible. In a similar manner, a tag 50 could be provided on the sterile packaging 14 surrounding a surgical instrument 12, so that the packaging tag could be read in order to read the data on a tagged surgical instrument inside the packaging.

The tag 48 may include CMOS technology and other circuitry to allow it to act as a transponder with respect to the surgical instruments 12, and may be an active tag and include a battery. In this case, the tag 48 may either be removably attached to the tray 14 so that it may be removed during the sterilization process or may be suitably protected, e.g. by thermally insulating packaging. This can be achievable for the tray tags 48 as the restrictions on them may be less onerous, and they can for example be larger and more easily handled than the instrument tags 12. Also, hospitals tend to use autoclave sterilization processes, rather than gamma ray processes, which are more usually employed by instrument manufacturers. Accordingly, the instrument tray tags 48 generally only need to be autoclave resistant rather than irradiation resistant. Also, they may be of larger size, and so may accommodate large thermal jacketing and the like, and are more easily handled.

Figures 4, 5:
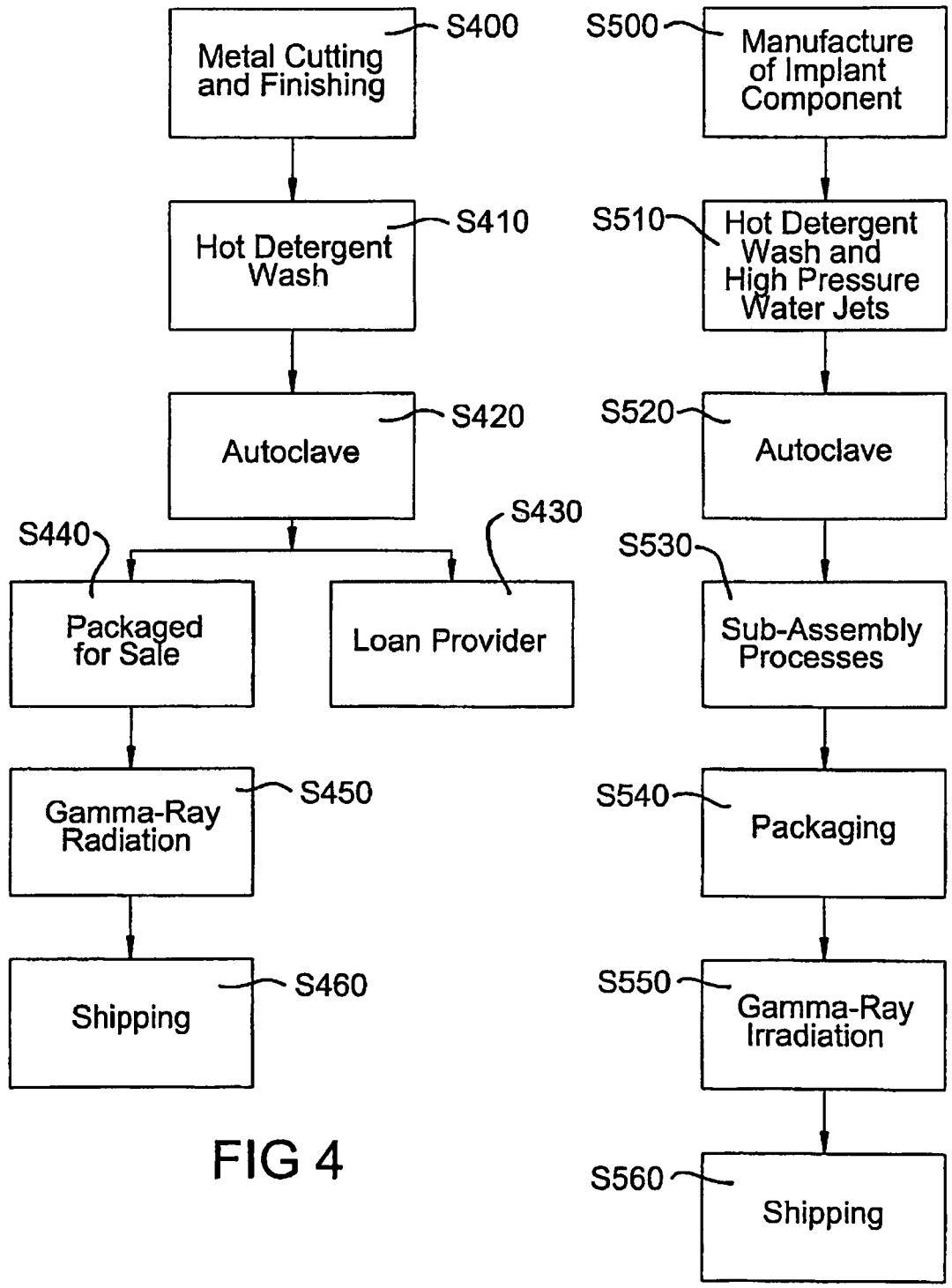
FIG. 4 is a flow chart of an instrument manufacturing process.
FIG. 5 is a flow chart of an implant manufacturing process.

FIG. 4 shows a typical manufacturing process for a surgical instrument, in which the instrument is formed at step S400, given a hot detergent wash at step S410 to remove grease, cutting oils and the like, sterilized by autoclaving at step S420, and then either sent to a loan provider (discussed below) at step S430 or packaged at step S440, e.g. in a sterile environment, and then subjected to gamma-ray irradiation at step S450 for a final sterilization and shipped out to suppliers and warehouses at step S460. In this process, an RFID tag 12 may be added at any suitable time. It may for example be added during forming of the instrument at step S400, so that it is embedded in the device, e.g. moulded into a plastics element or into a metal body, or it could be attached after forming, e.g. after washing and before or after autoclaving. Attachment could for example be by adhesive or a mechanical fastening. If adhesive is used, it should be appropriately autoclave and/or irradiation resistant. The packaging may also be tagged, although this may not be necessary if the packaging allows for the passage of RF signals, as the tagging of the instrument itself within the packaging may then be sufficient to allow for tracking of the packaged item. An active packaging tag including a transponder circuit may be used, so that it can read the instrument tag. In this case, the tag may be provided after gamma irradiation, and may be removable or autoclave resistant, e.g. may include a thermal jacket.

As well as surgical instruments, other hospital and medical equipment and supplies may be tagged. This would include for example implants, e.g. orthopaedic implants, e.g. artificial joints. Again, the tag could be attached during or after manufacture of the joint, and could be applied by adhesive or in a mechanical manner or through embedding the tag in the joint, e.g. during a moulding process. A typical manufacturing process is shown in FIG. 5, and includes in step S500 the forming of the implant, and in step S510, the cleaning and washing of the implant to remove grease and cutting oil, as well as in step S520 the sterilization of the implant by an autoclave process. The sterilized parts then undergo a sub-assembly process, if necessary, at step S530, and are packaged at step S540. The packaged implant is then gamma ray irradiated at step S550 and shipped out at step S560. Gamma irradiation may be especially useful in the implant manufacture process, due to its high penetration distance.

Again, the RFID tags used must be able to withstand the gamma radiation and preferably also the autoclaving process, and may be added at any suitable time in the process. Again, an RFID tag may be applied to packaging of the implant, and this tag may include a transponder for communicating with the implant tag.

Often, instead of having all of the necessary tools for an operation in-house, a hospital will effectively contract out the supply of the tools by ordering loaner kits from a kit provider. These kits will include all necessary tools for a particular operation, and will be shipped out to the hospital a day or two before the operation in which they are to be used. Such a system is especially popular in orthopaedic surgery, where an implant operation will generally use a number of tools that are especially designed and sized for the particular implant.

Figure 6:
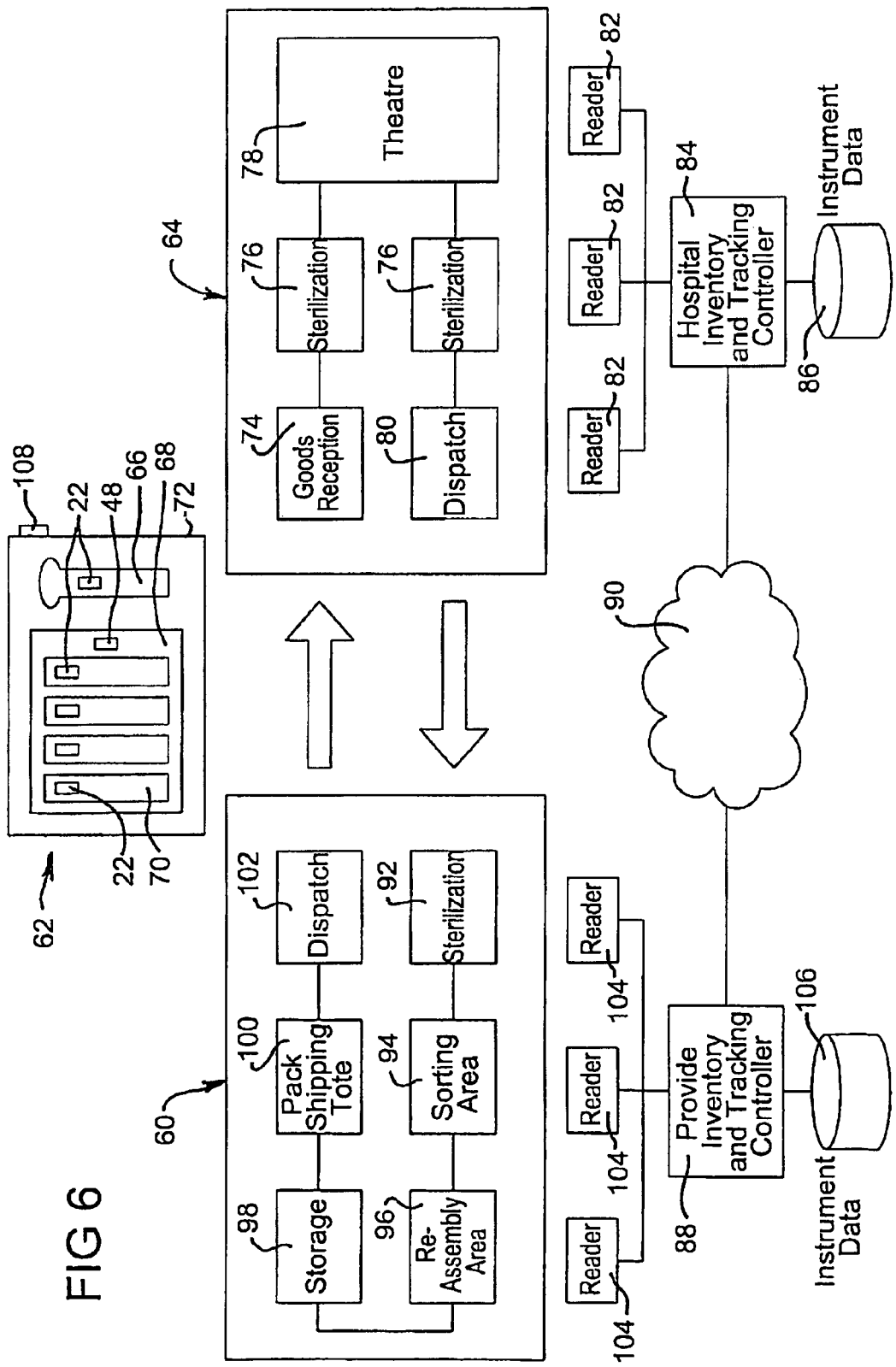
FIG. 6 is a schematic diagram of a loaner kit system.

FIG. 6 shows a schematic diagram of a loaner kit process, in which a loaner kit provider 60 provides a loaner kit 62 to a hospital 64. The loaner kit 62 includes an orthopaedic implant 66 and an instrument tray 68 on which are mounted a number of surgical instruments 70 for use in implanting the implant 66 in a patient. The instruments 68 could for example include jigs, drills, saws and reamers, as well as scalpels, scissors, forceps, and fastening elements, including screws, nuts, bolts, wire and the like.

Often, a surgeon will not know the exact type or size of implants 66 that are needed in an operation until surgery has begun, and the implant site has been inspected. Accordingly, a loaner kit 62 will generally include a number of implants 66. Also, for each size and type of implant 66, a different set of surgical instruments 68 of corresponding size and characteristics, will generally be required so as to ensure correct and accurate implantation of the implant 66. Therefore, the kit 62 will often be quite large in size and will include a large number of different items 66-70, which will be provided together in a sealed tote 72.

All of these items 66-70 need to be carefully controlled and inventoried, and so the use of the present RFID tagging system and micromechanical array RFID tags 22 are especially advantageous in this situation, as they enable both the provider 60 and the hospital 64 to keep track of the kits 62 and their parts 66-70. This can avoid losses, ensure that items are properly sterilized, ensure that proper sizes are coordinated, and ensure that no parts are missing before a surgery begins. Also, parts mounted in sterile packaging and the like can be checked for correctness before having to be opened.

As shown in FIG. 6, a kit 62 may be dispatched to the hospital 64, where it is acknowledged as received in the goods reception department 74. The kit is then sterilized in the central sterilization department or CSSD 76, and sent to the theatre 78 for use in an operation. During the operation, the surgeon will select the desired implants 66 and conduct the implant surgery. Used and unused instruments and implants are then placed back into the tote 66 and returned to the central sterilization department 78 for post-operative sterilization. Next, the kit 62 is shipped back to the kit provider 60 through the dispatch department 80. At each stage in the kit's progress through the hospital, the parts may be monitored by RFID interrogators 82 connected to a central inventory and tracking management controller 84, which can record the history of each tagged item, including its whereabouts, its usage and sterilization history, and the patients in relation to which it has been used.

Patient identification is an especially useful feature, as it allows for an effective instrument recall and destruction/sterilization procedure to be employed should a patient later be found to be infected in some particular manner. It would also allow other patients that have been operated on using the same instruments to be identified and informed.

Instrument history may for example be stored in a database 86, and data, instructions, information and the like may be swapped between the hospital inventory and tracking system 84 and the inventory and tracking controller 88 of the kit provider 60, e.g. over a suitable communications network 90, such as the Internet or a dedicated secure link.

When returned to the kit provider 60, the kit parts will be subject to sterilization in a sterilization department 92, and then passed to a sorting area 94 and a re-assembly area 96, where the parts are catalogued and re-assembled into full kits or into full kit units, e.g. a complete instrument tray for a particular implant. These kits and kit units are then placed in storage 98 ready for use in a new kit order from a hospital or the like, at which time the kits will be assembled and/or identified in the packing department 100 before being shipped out by the dispatch department 102.

As with the hospital inventory and tracking control 84, the provider inventory and tracking control 88 may communicate with a number of RFID interrogators/reader 104 throughout the various departments, so that the control 88 can keep a record of equipment used, e.g. in a database 106. The system can also assist in billing for items used or lost, for identifying and ordering replacement parts, for putting together kits and for checking to ensure that parts are consistent and that kits conform to hospital orders and requirements. It may also allow for the automated assembly of kits, as well as checking and verification processes.

The use of the present resonant member tags 22 for the instruments 70 and for the implants 66 enables the instruments and implants to undergo the sterilization processes, whilst still providing an effect tagging system. This sterilization will generally include autoclaving, and may also include gamma irradiation, although this is less likely to be a part of the loaner process and is more usually a part of the manufacturing process.

Not all parts of a kit 62 may need sterilization during the loaner process, and, for example, the implants 66 may be received by the loaner company in sterilized packaging, e.g. after having undergone gamma irradiation at the manufacturing stage, and may be passed to the hospital in the form received. These implants may then not require sterilization by the hospital either. Also, unopened equipment in sterilized containers that were not used during surgery may not need further sterilization, or may only need sterilization of their outer packaging.

The instrument trays 68 may again include their own RFID tags 48, which may read the instrument tags 22, and the tote 72 may also include an RFID tag 108, which may itself read the tray tags 48 and/or the instrument and implant tags 22. Thus, an RF reader 82 may read instrument or implant information from the tags 22 by interrogating the tag 108, which in turn will interrogate tags 68 or tags 22. This allows simple, small, robust and sterilization process resistant passive tags to be used with the instruments and implants, and more complex, larger and/or less resistant tags to be used for instrument and implant containers.

Although discussed above mainly in relation to surgical instruments for use in hospitals, the tagging systems and methods and the use of RFID tags with data stores of micromechanical resonant members has broader application, and may be used in any situation where an item needs to be both tagged and sterilized by an autoclaving and/or an irradiation process. The system may for example be used in relation to dentistry and veterinary applications. It may also be used to tag sterilized needles, e.g. prefilled needles, blood products and in other medical and healthcare applications. It may further be used outside of the medical and healthcare environments, e.g. in relation to foodstuffs, and general hygiene areas, and may be used in scientific research areas and laboratories, where sterilization may be required due to contamination concerns.

Figure 7:
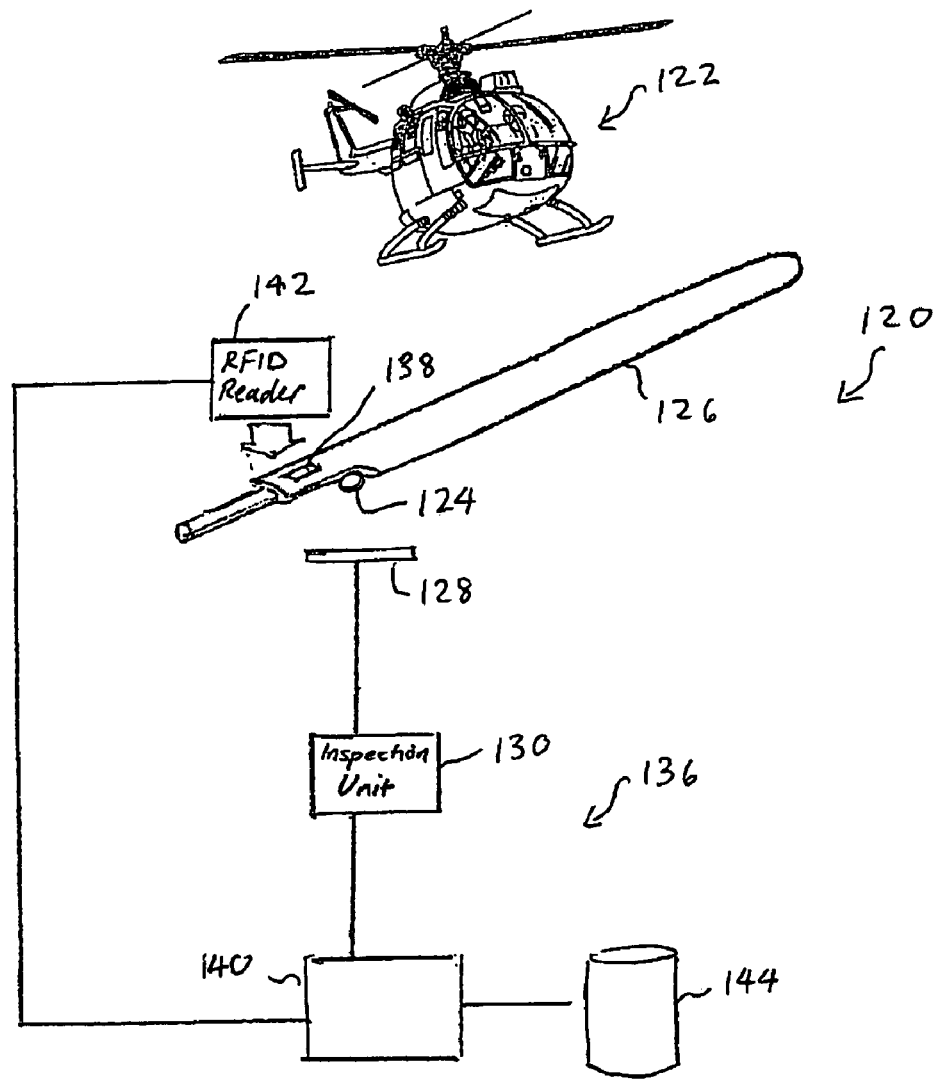
FIG. 7 is schematic diagram of an exemplary item inspection system.
Figure 8:
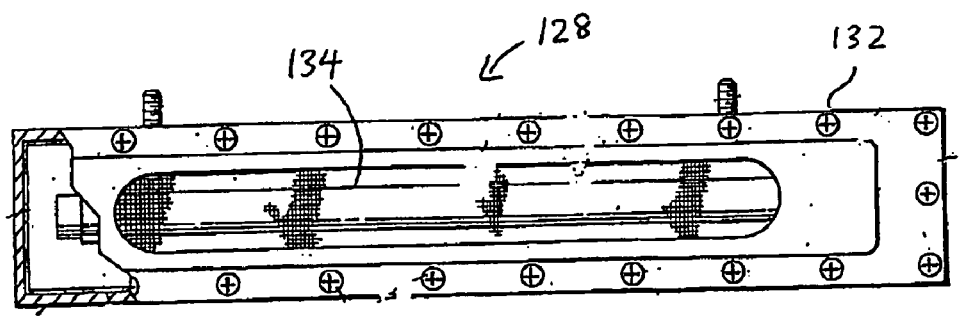
FIG. 8 is a plan view of a radiation detector forming part of the item inspection system of FIG. 7

FIG. 7 shows schematically an aircraft blade inspection system 120 for inspecting rotor blades intended for use with a helicopter 122. Aircraft blades are subject to severe stress and occasionally develop minute cracks. It is of critical importance that a crack in the blade be detected at an early time so that the blade may be replaced preventing an in-flight accident.

During routine helicopter maintenance, the rotor blades are removed from the helicopter 122 and are inspected via the inspection system 120. A pressure sensor 124 with a beta radiation source is mounted in each blade 126. The inspection system 120 includes a beta radiation detector 128 adapted to receive beta radiation from the beta radiation source within the pressure sensor 124 during inspection of the blade 126. The inspection system 120 also includes an inspection unit 130 containing electronic circuitry.

The pressure sensor 124 includes a member which moves as a function of the pressure within the blade 126 on which the sensor 124 is mounted. A beta radiation source is carried within the moving member and the member has a window which is blocked when the pressure on the blade 126 is in an acceptable range. If the pressure within the blade 126 reaches an unacceptable range, thereby indicating leakage through a crack in the blade 126, the member moves, unblocking the window such that radiation passes through the window and is detected by the beta radiation detector 128. Such a pressure sensor is described in U.S. Pat. No. 3,985,318.

As shown in FIG. 2, the beta radiation detector 128 includes a housing 132 in which is mounted a Geiger-Mueller tube 134. In operation, the beta particles from the source in the pressure sensor 124 pass through the housing 132 to the tube 134 when the sensor 124 passes over the detector 128. The electronic circuitry in the inspection unit 130 receives an output signal from the tube 134 indicative of the presence or absence of one or more cracks in the blade 126.

The blade inspection system 120 also includes an RFID tracking system 136 for identifying and tracking the various blades inspected. The tracking system 136 can notably monitor when and which blades have been inspected for defects. This may be done by tagging each blade with an RFID tag 138 and by having a central controller 140 in communication with an RFID interrogator 142 provided at an appropriate location. Blades that have passed through inspection can be interrogated by the interrogator 142, and the data response of the RFID tag 138 can then be read and can be recorded by the central controller 140 in a database 144.

The RFID tag 138 includes data arrays formed of micromechanical resonant members. The use of the resonant members as data carriers allows the RFID tag 138 to withstand beta radiation inadvertently received from the source in the pressure sensor 124, whilst remaining compact in size and allowing for RF communication. It does away with the need for vulnerable microprocessors and CMOS circuitry.

It will be appreciated that the aircraft blade inspection system 120 is merely one illustrative example of an inspection system in which items are subject to ionizing radiation in a non-sterile environment, and is which items being sterilised can be tracked by an RFID device including a data store formed by micromechanical resonant members that respond to an applied RF interrogation signal with a data response. Similarly systems exist for inspecting sections of railway track, propeller shafts, turbine blades and other items including metallurgical components, and the present invention is suitable for use in identifying and tracking items in each of these inspection systems.

It will be further appreciated that many systems exist in which items requiring to be identified and tracked are subject to ionizing radiation without necessarily inspected for structural integrity. This situation arises where items are intended for use with or forming at least part of artificial satellites, spacecraft, aircraft, nuclear power stations and nuclear weapons. Once again, the present invention is suitable for use in identifying and tracking such items.

Various alterations, additions and/or modifications may be made to the parts previously described without departing from the ambit of the present invention, and that, in the light of the above teachings, the present invention may be implemented in a variety of manners as would be understood by the skilled person.

The present application may be used as a basis for priority in respect of one or more future applications, and the claims of any such future application may be directed to any one feature or combination of features that are described in the present application. Any such future application may include one or more of the following claims, which are given by way of example and are non-limiting with regard to what may be claimed in any future application.

The invention claimed is:

1. A method of tagging and sterilizing an item, the method including the steps of:
providing an item that is to be sterilized and tagged;
applying an RFID tagging device to said item, said tagging device including a data store formed from an array of micromechanical resonant members, said resonant members being configured to vibrate in accordance with an applied RF signal, so as to provide a data response; and
sterilizing said tagged item by autoclaving or by irradiation.

2. The method of claim 1, wherein said sterilization step includes autoclaving the tagged item at a temperature of 120° C. or above.

3. The method of claim 1, wherein said irradiation step includes the irradiation of the tagged item by gamma radiation.

4. The method of claim 3, wherein said irradiation step includes the step of applying a dosage of 2.5 Mrads or more of gamma radiation to said tagged item.

5. The method of claim 1, wherein said irradiation step includes the irradiation of the tagged item by beta radiation.

6. The method of claim 1, wherein said resonant members are configured for vibration under a Lorentz force.

7. The method of claim 1, wherein said RFID device is encased in an autoclave and/or irradiation resistant outer cover.

8. The method of claim 1, wherein said RFID device includes support circuitry for said resonant members formed from autoclave and/or irradiation resistant components.

9. The method of claim 1, wherein said RFID device includes support circuitry for said resonant members including Schottky diodes.

10. The method of claim 1, wherein said tagged item is a medical or healthcare item.

11. The method of claim 1, wherein said tagged item is a surgical instrument or a surgical implant.

12. The method of claim 1, wherein said tagged items are provided in a container, said container including an RFID tag thereon.

13. The method of claim 12, wherein said container RFID tag includes a transponder for communicating with said tagged items, and wherein said container RFID tag is provided in a thermally protective housing and/or is removably mounted on said tray.

14. The method of claim 12, wherein said container tag is an active tag and said item tags are passive tags.

15. The method of claim 1, wherein said tagged items are parts of a loaner kit of surgical equipment to be loaned to a hospital by a loaner kit provider.

16. The method of claim 1, wherein said resonant members are configured for vibration under a Lorentz force.

17. The method of claim 1, wherein said RFID device is encased in an irradiation resistant outer cover.

18. The method of claim 1, wherein said RFID device includes support circuitry for said resonant members formed from irradiation resistant components.

19. A system of tracking RFID tagged items through a process including a sterilization of said tagged items by an autoclave or irradiation process, the system including an inventory controller in communication with one or more RFID readers for reading said tagged items, wherein said items are tagged by RFID devices, a said RFID device including a data store formed by micromechanical resonant members that respond to an applied RF interrogation signal with a data response.

20. A sterilized and RFID tagged item, wherein said RFID tag includes a data store formed from an array of micromechanical resonant members, said resonant members vibrating in accordance with an applied RF signal, so as to provide a data response; and wherein said sterilization was by autoclaving or by irradiation of said tagged item whilst said item was tagged.

* * * * *